(12) United States Patent
Leinenbach et al.

(10) Patent No.: US 9,782,531 B2
(45) Date of Patent: Oct. 10, 2017

(54) MEDICAL SEPARATING DEVICE

(75) Inventors: Hans-Peter Leinenbach, Krems-Rehberg (AT); Franz-Josef Gerner, St. Wendel (DE); Stefan Kuhn, Neunkirchen (DE); Ekkehard Schinzel, Neunkirchen (DE); Patrick Priesnitz, St. Wendel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 602 days.

(21) Appl. No.: 13/881,841

(22) PCT Filed: Oct. 18, 2011

(86) PCT No.: PCT/EP2011/005218
§ 371 (c)(1),
(2), (4) Date: Jun. 27, 2013

(87) PCT Pub. No.: WO2012/055500
PCT Pub. Date: Mar. 3, 2012

(65) Prior Publication Data
US 2013/0270198 A1    Oct. 17, 2013

(30) Foreign Application Priority Data

Oct. 29, 2010 (DE) .................. 10 2010 049 790

(51) Int. Cl.
*G01N 30/56* (2006.01)
*B01D 15/20* (2006.01)
(Continued)

(52) U.S. Cl.
CPC ............ *A61M 1/36* (2013.01); *A61M 1/3679* (2013.01); *B01D 15/206* (2013.01); *B01D 15/22* (2013.01);
(Continued)

(58) Field of Classification Search
CPC ...... B01D 29/908; B01D 15/18; B01D 15/20; B01D 15/206; B01D 15/22; G01N 30/56;
(Continued)

(56) References Cited

U.S. PATENT DOCUMENTS 3,459,307 A * 8/1969 Collins, Jr. ............ B01D 29/05
210/316
4,247,987 A * 2/1981 Coulaloglou et al. .......... 34/249
(Continued)

FOREIGN PATENT DOCUMENTS

DE      3633583      4/1987
DE      8915876      9/1992
(Continued)

*Primary Examiner* — David C Mellon
(74) *Attorney, Agent, or Firm* — Jacobson Holman, PLLC.

(57) ABSTRACT

A medical separation device, its production, and its use are provided, wherein the device has a hollow cylindrical housing sealed at its top and bottom sides, wherein the device has an outer wall, a fluid inlet, and a fluid outlet, and wherein the device has a filling connection for a separation medium arranged tangentially to, and inside of, the cylindrical housing outer wall for filling the device with a separation medium.

8 Claims, 6 Drawing Sheets

(51) Int. Cl.
   *B01D 15/22* (2006.01)
   *G01N 30/60* (2006.01)
   *A61M 1/36* (2006.01)

(52) U.S. Cl.
   CPC ........... *G01N 30/56* (2013.01); *G01N 30/606* (2013.01); *G01N 2030/562* (2013.01); *Y10T 156/1062* (2015.01)

(58) Field of Classification Search
   CPC .. G01N 30/60; G01N 30/6052; G01N 30/606; G01N 30/6017; G01N 30/6026; G01N 30/6004; G01N 2030/562; A61M 1/36; A61M 1/3679; A61M 1/3675; A61M 1/3687; A61M 1/0094
   See application file for complete search history.

(56) References Cited

U.S. PATENT DOCUMENTS

| | | | |
|---|---|---|---|
| 4,627,918 A * | 12/1986 | Saxena | B01D 15/14 210/198.2 |
| 4,722,786 A | 2/1988 | Weaver | |
| 4,927,536 A * | 5/1990 | Worrell | B04C 5/26 209/729 |
| 4,946,047 A * | 8/1990 | Kurokawa | B01D 29/33 137/549 |
| 5,186,826 A | 2/1993 | Otto et al. | |
| 5,667,676 A * | 9/1997 | Alaska | B01D 15/206 210/198.2 |
| 6,498,007 B1 | 12/2002 | Adachi et al. | |
| 7,208,085 B2 * | 4/2007 | Geng | B01D 15/206 210/198.2 |
| 8,778,187 B2 * | 7/2014 | Gebauer | B01D 15/206 210/198.2 |
| 2005/0145573 A1 | 7/2005 | Nanko et al. | |
| 2007/0276351 A1 | 11/2007 | Nilsson | |
| 2009/0321338 A1 | 12/2009 | Natarajan | |
| 2010/0189602 A1 | 7/2010 | Baeuerie et al. | |
| 2011/0262300 A1 | 10/2011 | Rahn et al. | |

FOREIGN PATENT DOCUMENTS

| | | |
|---|---|---|
| DE | 19540431 | 7/1997 |
| DE | 102008053131 | 4/2010 |
| EP | 0 106 419 | 4/1984 |
| EP | 0507245 | 5/1995 |
| GB | 2181073 | 4/1987 |
| WO | WO 99/36110 | 7/1999 |

* cited by examiner

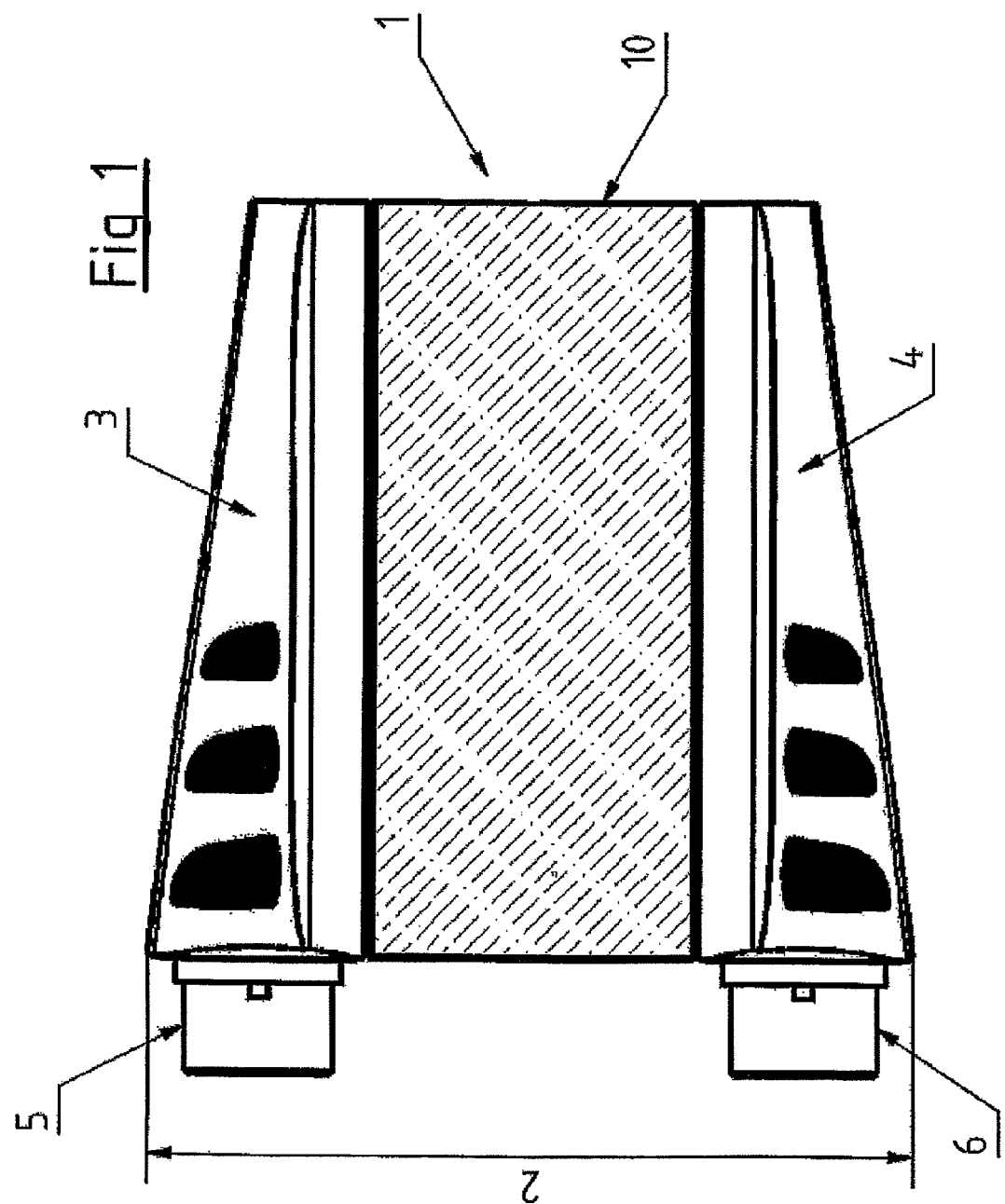

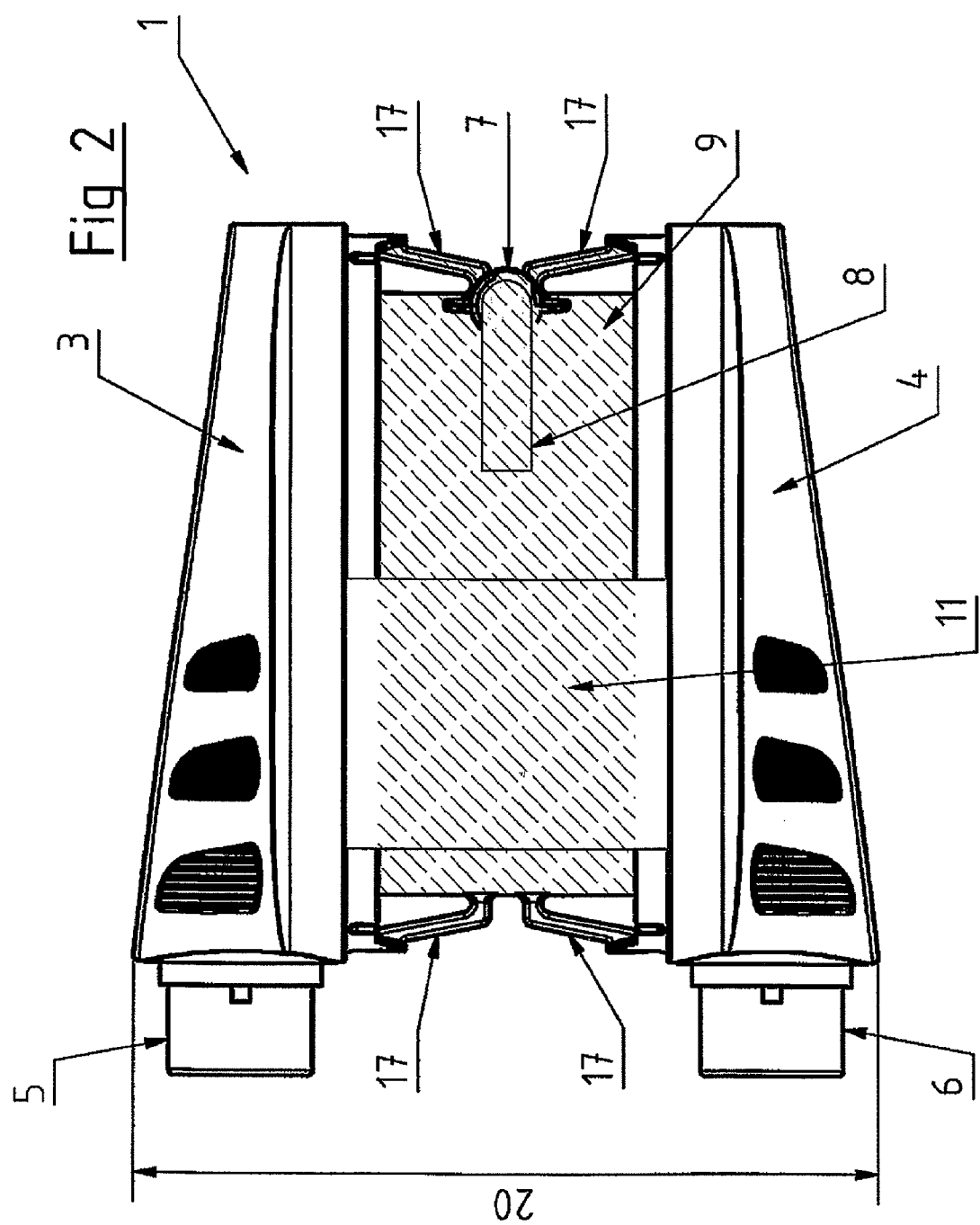

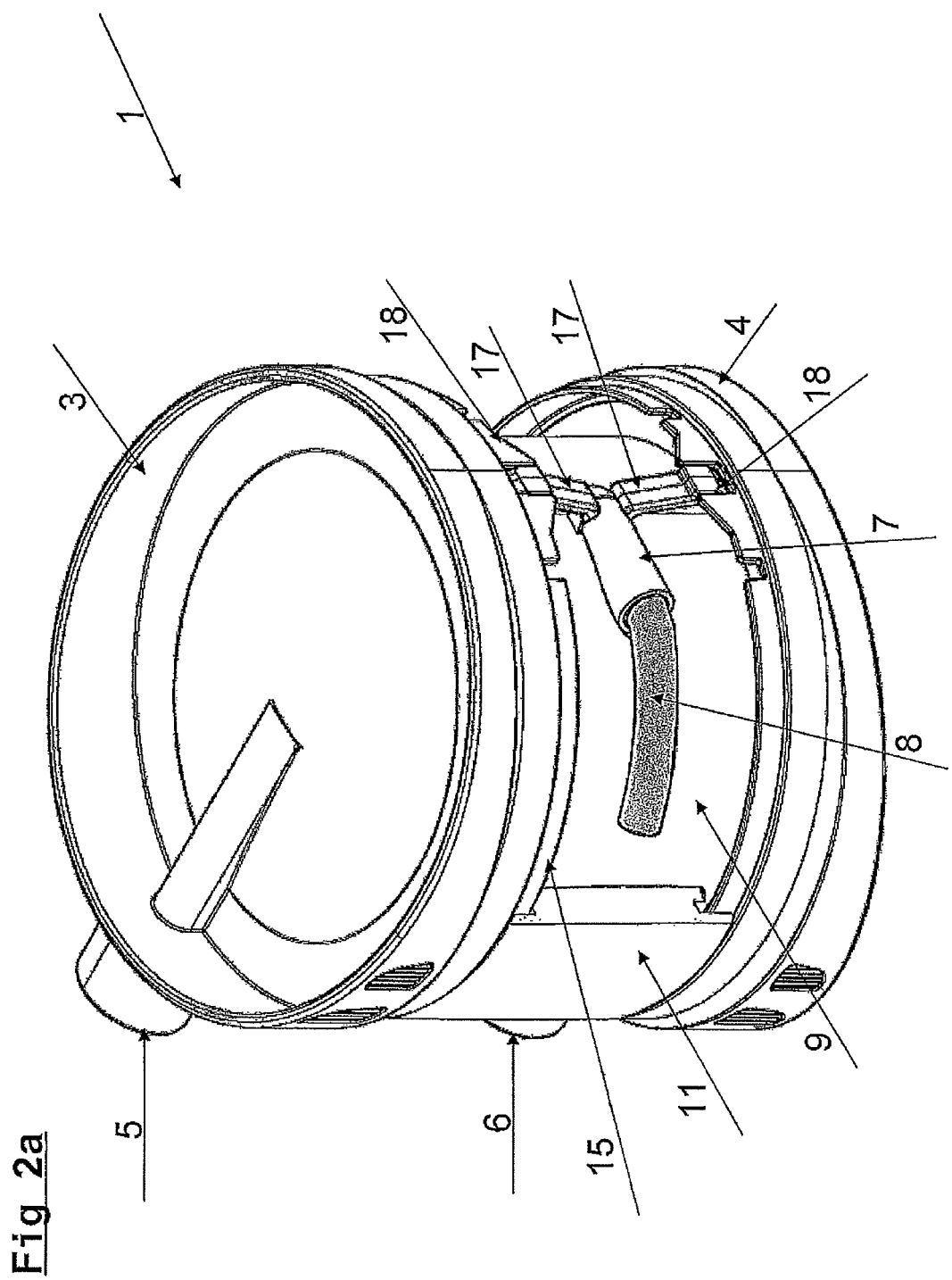

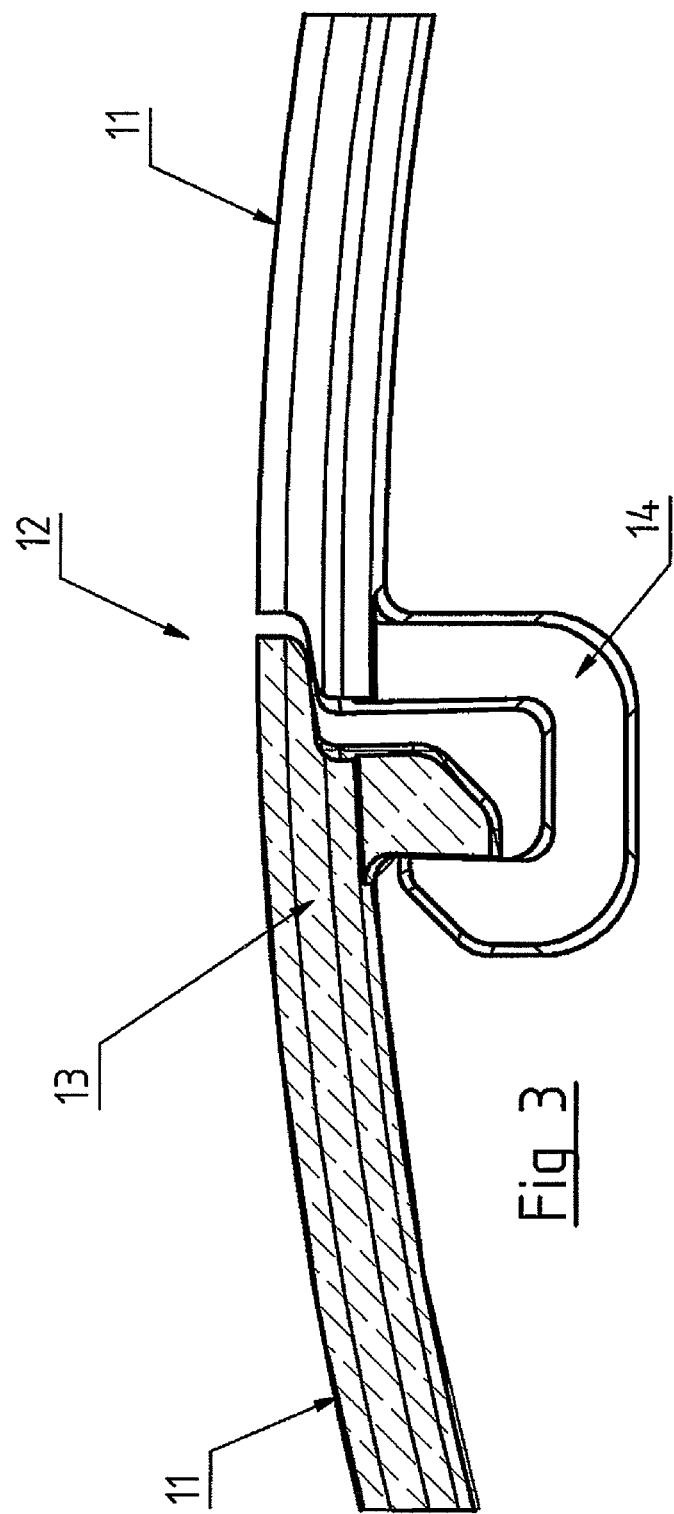

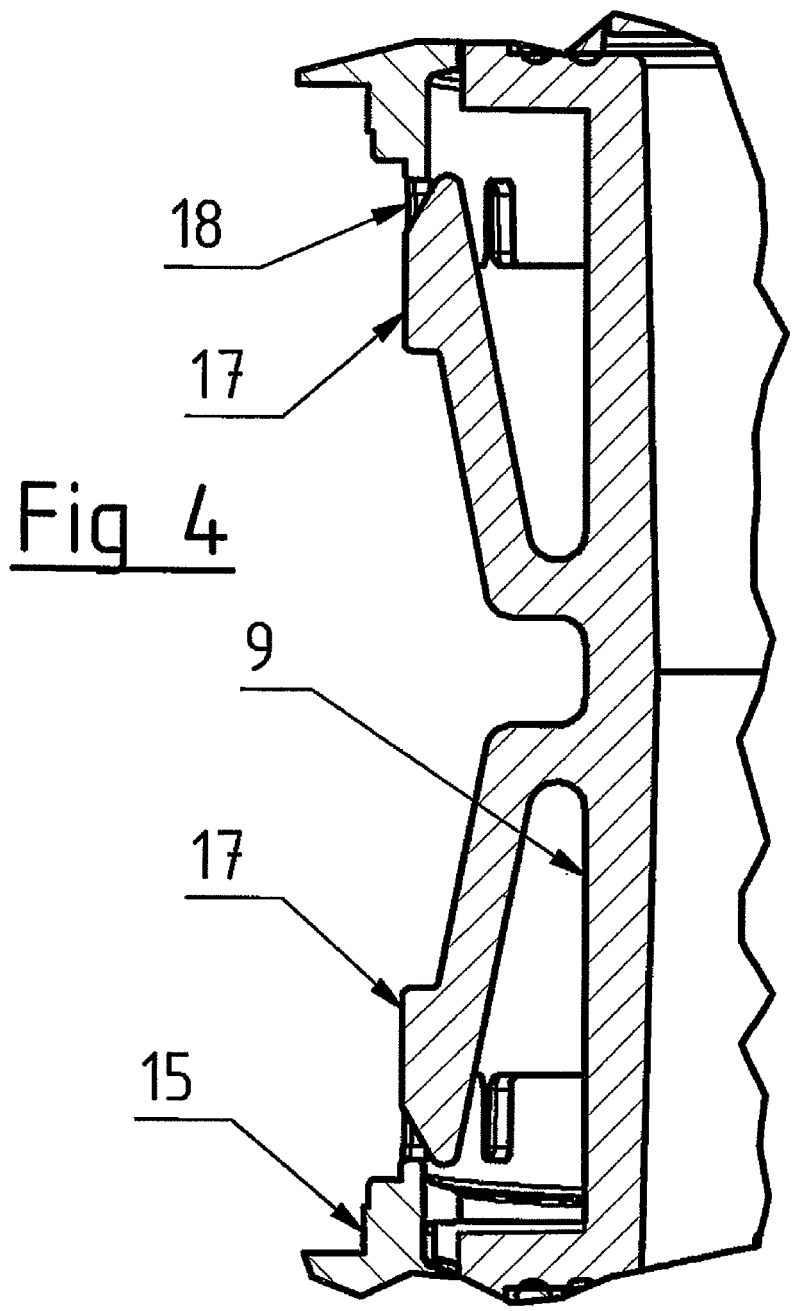

MEDICAL SEPARATING DEVICE

This is a national stage of PCT/EP11/005218 filed Oct. 18, 2011 and published in German, which has a priority of German no. 10 2010 049 790.8 filed Oct. 29, 2010, hereby incorporated by reference.

The invention relates to medical separation devices consisting of a hollow cylindrical housing, where the housing is closed at the top and bottom sides and has a fluid inlet and a fluid outlet as well as filling connections for a separation medium. The separation device is also suitable for use in technical, analytical or pharmaceutical fields.

Various treatment methods in which medical separation devices, in particular adsorbers are used are known from the state of the art. For example, systems using either a small-volume housing or a complex larger housing made of glass are used in immunopheresis. The adsorbers used may be filled with the separation medium or adsorber medium via a radial inlet line and sealed with a sealing plug. Since the radial inlet line protrudes out of the housing, there is the risk that it may be damaged, for example, due to being dropped, an impact or some other external interfering influences. As a result, the separation device may lose its tightness and/or sterility.

It is also a disadvantage that the sealing plug is not protected from improper handling because there is the possibility of opening the sealing plug due to its easy accessibility. The adsorber may be connected improperly to the patient line or the tightness and/or stability of the adsorber may be lost due to opening of the sealing plug.

With existing systems having a radial filling connection, this connection is sealed with a sealing plug after being filled. Such a design necessitates a suitable length of the filling connection, so that filling with the separation medium and sealing with the stopper are successful. This results in another deleterious aspect because the ratio of the housing length to the length of the filling connection becomes even more unfavorable as the diameter of the housing is smaller. This counteracts the effort to achieve a compact design of the adsorber housing. A compact design should be characterized in that the separation device requires the least possible amount of space, a minimum of repackaging and a minimum of shipping and storage space.

With some adsorber models, there is also the risk that they can be dismantled completely because the screw cover and/or bottom covers is/are not secured separately. Therefore, the authenticity of such a separation device is not ensured over its entire lifecycle.

The deleterious factors described here result in the fact that safety cannot be guaranteed absolutely when using the separation device on a patient.

In addition, various methods for how the adsorber together with the separation medium may be used are also known from the state of the art.

DE 10 2008 053 131 A1 describes an arrangement for sterilizing a final package, in particular an adsorber in which the final package is connected to an adsorber housing via a radial inlet line. The separation medium is stored in the final package. After sterilization, the adsorber housing and the final package form a sterile unit via the radial inlet line. This arrangement allows transfer of the separation medium into the adsorber housing in a sterile environment at a given time.

In another method, the adsorber housing may be filled directly with a separation medium. Following the filling, sterilization of the filled separation device by means of high-energy ionizing radiation is necessary, for example, alpha-, beta- or gamma-radiation.

EP 0 507 245 B1 describes a device for separating biological materials in which the inlet tube for the solution to be separated is preferably mounted on the side.

The object of the present invention is to make available medical separation devices in which the housing of the separation devices has a filling connection at the side for filling it with a separation medium and has a compact housing design, which also leads to a reduction in the possible repackaging as well as transport and storage space and thus results in cost savings.

In addition, the invention should be characterized in that through structural elements on the housing, the authenticity of the latter is guaranteed and thus its safety in use of the separation device for the patient is increased.

With the separation device according to the invention it should also be possible for the latter to be filled directly with the separation medium and to be sterilized. Furthermore, the invention should also include a partially prefabricated housing having a separate container, which contains the separation medium, so that the final filling of the housing can occur after sterilization of the housing, the tubing system and the separation medium in an unsterile environment.

For the separation device according to the invention, the individual components should be designed to be as functional as possible in order to be able to install them in a rapid and inexpensive method and to provide the user with a separation device that is easy to handle.

This object is achieved according to the present invention by the features of the separation device, its manufacture, and its use described and claimed below, in that the filling connection for the separation material is attached to the housing tangentially. Advantageous embodiments of the invention are the subject matter of the following description and claims.

The device according to the invention is explained in greater detail below with reference to the drawings.

FIG. 1 shows the external design of the separation device.

FIG. 2 and FIG. 2a show the internal design of the separation device from different perspectives, showing the tangential filling connections at the side, housing end caps and mounting elements for attaching the housing end caps.

FIG. 3 shows a catch mechanism for connecting the exterior wall segments of the housing.

FIG. 4 shows a detailed diagram of the mounting elements on the inside wall of the housing and the housing end caps with a peripheral furrow or groove.

Figure 5:
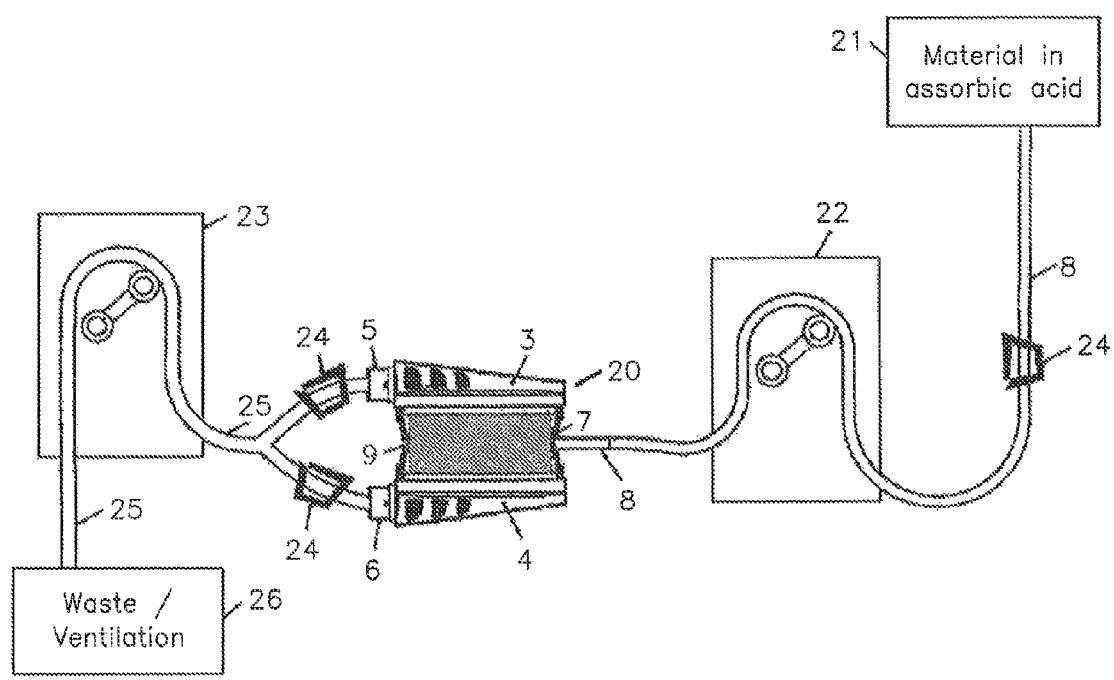
FIG. 5 shows, for example, a schematic diagram of the method for filling the separation device with the separation medium.

The design of the medical separation device (1), as shown in FIGS. 1, 2 and 2a, consisting of a hollow cylindrical housing (2), which is sealed on the top and bottom sides by housing end caps (3, 4), has a fluid inlet (5), a fluid outlet (6) and a filling connection (7) for filling the medical separation device (1) with the separation medium, which may also be referred to as the adsorbent or stationary phase, where the filling connection (7) is attached tangentially to the essentially round, in particular cylindrical, bulbous, concave or convex medical separation device (1).

A hose line (8) may be connected to the filling connection (7) in a wide variety of ways to establish a fluid connection between a separate container or storage container (not shown), which is filled with the separation medium, and the filling connection (7). The hose line (8) may preferably be welded, connected, plugged or screwed onto or inserted into the filling connection (7). After adding the separation medium, the hose line (8) between the container and the device (1) according to the invention may be cut to a suitable length and sealed.

In a preferred embodiment, a lateral tangential arrangement of the filling connection (7), in particular on the inner housing (9), allows a compact and space-saving design.

To be able to implement such a design of the separation device (1) according to the invention, the tangential filling connection (7) protrudes by a length between 0 and 20 mm, preferably 0 to 18 mm, especially preferably to 16 mm from the inner housing (9). The inner housing (9) itself has a diameter of 3 to 15 cm, preferably 4 to 12 cm, especially preferably 5 to 10 cm.

In order for the inner housing (9) and the filling connection (7) to be in a balanced relationship to one another, the ratio of the diameter of the inner housing (9) to the length of the filling connection (7) protruding out of the inner housing (9) is up to 7.5/1, preferably up to 6.7/1, especially preferably up to 6.25/1.

In another preferred embodiment, the remainder of the hose line (8) remaining on the filling connection (7) may be placed conveniently around the inner housing (9).

To protect the filling connection (7) and the hose line (8) from external influences, in an especially preferred embodiment, a housing outer wall (10) may be placed in front of an inner housing (9), which also contributes to the compactness and safety of the medical separation device (1).

To be able to enclose the inner housing (9) including the filling connection (7), which protrudes out of the inner housing (9) by a housing outer wall (10), the distance between the inner housing (9) and the housing outer wall (10) amounts to 2.0 to 10 mm, preferably 3.5 to 8 mm, especially preferably 4.5 to 6.8 mm.

The housing outer wall (10) may be composed of housing outer wall segments or panels (11). The housing outer wall (10) preferably consists of two, four or six housing outer wall segments (11), which preferably surround or are placed in front of the inner housing (9) of the separation device (1).

To be able to join the individual housing outer wall segments (11) to one another, they have a catch mechanism (12) like that shown in FIG. 3, which is preferably situated on the outer sides of the housing outer wall segments (11). The catch mechanism (12) may be embodied in the form of clip, snap or hook connections. It is self-evident that each housing outer wall segment (11) has at least one catch element (13) and at least one receiving element (14).

If the inner housing (9), including the filling connection (7) and the hose line (8), has cladding in the form of a housing outer wall (10), preferably housing outer wall segments (11), offers the advantage that no radially protruding filling line or closure cap need be present on the outside of the device (1) according to the invention. If the separation device (1) is accidentally dropped, the filling connection (14), because it is behind the housing outer wall (10), is protected from damage due, for example, to breaking off or chipping of the filling connection (7) or a part thereof. The separation device (1) is still protected by the housing outer wall (10) from other destructive external influences, for example, the effects of an impact. Due to the fact that the housing outer wall (10) also covers the hose line (8) and thus no longer has any outwardly protruding closure cap, this prevents, for example, improper handling, faulty connection of the separation device (1) to the patient line or removal of the closure cap can be prevented. These structural measures ensure the authenticity of the separation device (1) and lead to an increased reliability when used on a patient.

In another especially preferred embodiment, the housing outer wall (10), preferably the housing outer wall segments (11), may be clamped or locked between upper and lower housing end caps (3, 4). The housing end caps (3, 4) are preferably designed to receive the housing outer wall (10), preferably the housing outer wall segments (11), in the form of a peripheral furrow or groove (15). This embodiment is illustrated in FIGS. 2 and 4.

In this case, the dimensions of the inner housing (9) and the filling connection (7) are to be selected so that together they are smaller than the radius of the housing end caps (3, 4), so that enough space remains to place a housing outer wall (10) in front. The size of the housing end caps (3, 4) depends on the aforementioned dimensions of the individual components.

With the separation device (1) according to the invention, it is also provided that the top side and the bottom side of the separation device (1) are closed by housing end caps (3, 4), as shown in FIGS. 1 and 2. The housing end caps (3, 4) may be plugged or screwed onto the housing (2), preferably the inner housing (9). The fluid inlet (5) and the fluid outlet (6) are preferably arranged radially in the housing end caps (3, 4).

In a preferred embodiment, the separation device (1) is designed so that the radial fluid inlet (5) and the radial fluid outlet (6) point in a predetermined direction, with the fluid connections (5, 6) especially preferably being arranged one above the other.

For the embodiment of the housing end caps (3, 4) having a screw closure, the position of the start of the thread on the housing (2) or on the inner housing (9) and on the housing end caps (3, 4) is crucial. The position of the start of the thread is to be selected so that the radial fluid inlet (5) and the radial fluid outlet (6) can be brought into a predetermined direction, preferably by arranging them one above the other.

If the housing end caps (3, 4) are plugged on the housing (2) or the inner housing (9), the plug-in device is to be designed according to the knowledge of those skilled in the art, so that the alignment of the fluid connections (5, 6) described above can be implemented.

An additional improved security of the separation device (1) can be achieved by the fact that mounting elements (17) for attaching the upper and lower housing end caps (3, 4) are preferably provided on the inner housing (9). The mounting elements (17) may be designed in the form of clip, snap or hook connections. At least one, preferably two or more mounting elements (17) are provided on the inner housing (9), especially preferably being mounted in pairs. The mounting elements (17) may also be aligned vertically opposite one another. Receiving elements (18) in the form of recesses, indentations or other possible designs to secure the housing end caps (3, 4) tightly and securely, preferably on the inner housing (9), are preferably situated opposite the mounting elements (17) in the housing end caps (3, 4), preferably in the edge area of the housing end caps (3, 4).

The embodiment described above has the advantage that the authenticity of the device is ensured because the housing end caps (3, 4) cannot be removed nondestructively from the housing (2) or the inner housing (9), thereby improving safety in use on patients.

Due to being locked on the housing (2), preferably on the inner housing (9), by means of the mounting elements (17) and locked on the housing end caps (3, 4) by means of the receiving elements (18), it is also possible to align the radial fluid inlet (5) and the radial fluid outlet (6) in a predetermined direction, preferably in such a way that the radial fluid inlet (5) and the radial fluid outlet (6) are arranged above one another.

Such an embodiment allows a simple assembly and at the same time an improved tightness because the individual parts of the device (1) experience a uniform prestress due to the holding mechanism and the individual components of the separation device (1) can be connected to one another with a great tightness.

The embodiments described above lead to a simplification in production and assembly because identical parts that do not make different requirements of assembly of the separation device (1) according to the invention and offer the user a device that is easy to handle in which the user need not pay attention to a particular direction of installation of the separation device (1) in the device may be used.

In addition, the invention comprises a method for manufacturing a housing for a medical separation device (1), preferably an adsorber housing having a filling connection (7) arranged tangentially on the housing, such that the filling connection (7) is preferably mounted laterally on the inner housing (9) of the separation device (1). The hollow cylindrical housing (2) is closed by upper and lower housing end caps (3, 4), such that the housing end caps (3, 4) are plugged or screwed onto the inner housing (9). The screw thread is designed, so that both the radial fluid inlet (5) and the radial fluid outlet (6), which are arranged in the housing end caps (3, 4), may be aligned in a predetermined direction. The housing end caps (3, 4) are preferably installed in such a way that the radial fluid inlet (5) and the radial fluid outlet (6) are arranged one above the other.

To be able to install the housing end caps (3, 4) tightly and securely, they are connected to the mounting elements (17). For fixation of the housing end caps (3, 4), at least one, preferably two or more mounting elements (17) are provided. With regard to simple assembly, it is advantageous to attach the housing end caps (3, 4) in such a way that they can be connected to the mounting elements (17) arranged in pairs vertically opposite one another on the inner housing (9). The housing end caps (3, 4) are locked on the inner housing (9) by the mounting elements (17) in the form of a clip, snap or hook connection. Receiving elements (18) in the form of recesses, indentations or other possible embodiments into which the mounting elements (17) may be fitted or locked are situated opposite the mounting elements (17) in the housing end caps (3, 4), preferably in the edge area of the housing end caps (3, 4).

In an especially preferred embodiment, the mounting elements (17) and the receiving elements (18) may be attached in such a way that the alignment of the radial fluid inlet (5) and of the radial fluid outlet (6) points in a predetermined direction, in particular such that the radial fluid inlet (5) and the radial fluid outlet (6) are arranged above one another.

Separation elements are usually used in the hollow cylindrical housing (2) and/or in the housing end caps (3, 4), these separation elements usually being screens or meshes, which may be applied to a supporting structure for stabilization and which serve to delineate the separation medium in a predefined space and ensure the most optimal possible fluid distribution.

A hose line may be mounted on the filling connection (7) in a first partially fabricated separation device (20) consisting of an inner housing (19), housing end caps (3, 4) and separation elements that are possibly required in the interior of the separation device (20). The hose line (8) may be welded, plugged or preferably inserted into the filling connection (7) in the sense of a simple process management. Other variants are of course also conceivable to connect the container where the separation medium is kept to the filling connection (7) of the inner housing (9) of the partially fabricated separation device (20).

After filling the partially fabricated separation device (20) with the separation medium, the hose line (8) is cut off at a suitable length and sealed. The open end of the hose line (8) may be closed off using a clamping mechanism, a stopper or with cutoff elements by some other suitable method. With regard to simple and inexpensive production of the partially fabricated separation device (20), it is preferable to cut off the hose line (8) by welding and to seal it in a sterile manner at the same time. The remainder of the hose line (8), which is still situated on the filling connection (7), may then be conveniently placed around the housing inside wall (9). The length of the tubing is preferably selected, so that it ends before the next mounting element (17).

In another method step, the housing outer wall (10), preferably in the form of housing outer wall segments (11), is arranged around the inner housing (9). A furrow or groove (15) into which the housing outer wall (10) or the housing outer wall segments (11) can be fitted is preferably provided in the housing end caps (3, 4). The housing outer wall (10) is preferably composed of at least two housing outer wall segments or panels (11). The individual housing outer wall segments (11) are connected to one another by a catch mechanism (12). For this purpose, catch elements (13) and receiving elements (14) in the form of clip, snap or hook connections (11) are preferably provided on the outsides of the housing outer wall segments (11). Each individual housing outer wall segment (11) is connected to the other(s) in alternation via at least one catch element (13) as well as via at least one receiving element (14) and they are fitted into or preferably locked with the housing end caps (3, 4). For stabilization, spacer elements (19) corresponding essentially to the distance between the inner housing (9) and the housing outer wall (10) and/or the outer wall segments (11) are provided at regular intervals on the housing outer wall (10) or the outer wall segments (11).

The separation device (1), which is now completely surrounded by the housing outer wall (10) or the housing outer wall segments (11), is then subjected to a sterilization by means of steam or high-energy ionizing radiation, for example, UV, x-ray, alpha, gamma or electron-beam radiation if it is provided as an adsorber for use on a patient, for example.

In another preferred embodiment, the partially fabricated separation device (20) is designed so that the housing outer wall (10) consists of two housing outer wall segments (11), such that one housing outer wall segment (11) is already premounted so that after filling with the separation medium and welding the hose line (8) it is only necessary to fit the last housing outer wall segment (11) in place. The separation device (1) fabricated in this way is also to be subjected to sterilization as described above before being used on a patient.

In a second preferred embodiment, the separation medium may be stored in a separate compartment or container (21) and connected to the partially fabricated separation device (20) by a hose line (8). The container (21) filled with the separation medium as well as the partially fabricated device (26) may first be sterilized together, to which end the separation medium may be transferred to the partially fabricated device (20) in due course. In this case, the separation medium may also be transferred to the partially fabricated separation device (20) even in an unsterile environment because the sterile unit of the separation device (20) and the container (21) remains untouched. After cutting off and welding the hose line (8), here again the housing outer wall (10) or the last housing outer wall segment (11) may be fitted into place.

FIG. 5 shows as an example the filling method of a partially fabricated medical separation device (20). The separation medium may be present in a separate compartment or container (21). This is connected to the tangentially arranged filling connection (7) on the inner housing (9) by means of a hose line (8). The adsorber material or separation medium is pumped by a pump (22) into the inner housing (9) of the partially fabricated separation device (20). When the filling operation is concluded, the fluid stream (8) is interrupted and the pump (22) is removed. Any residual air that may remain in the inner housing (9) is removed with a pump (23), which may be connected to the inner housing (9) via the fluid inlet (5) and/or via the fluid outlet (6) by pumping this air out through the filling connection (7). This permits airless filling of the housing. The fluid paths may be opened or closed by means of the hose clamps (24) accordingly. Next the hose line (8) is cut off at a suitable length at the filling connection and is closed off. In a preferred process management, the hose line (8) is cut off by welding and is sealed in a sterile manner at the same time. The hose system (25) including the pump (23) with the container (26) is removed. The piece of hose line (8) remaining on the filling connection (7) is placed around the inner housing (19), preferably as far as the nearest mounting element (17), and the last missing housing outer wall segment (11) is inserted.

The separation device (1) according to the invention is suitable for use in the technical, preferably analytical, medical and pharmaceutical fields.

The separation device (1) serves in particular to reduce the concentration of substances from a substance mixture, preferably for reducing the concentration of peptides or proteins, especially preferably cytokines, low-density lipoproteins (LDL), toxic foreign proteins, for example, animal toxins. In addition, the device (1) serves to reduce the concentration of antibodies, which may be either endogenous or exogenous antibodies, for example, therapeutically active antibodies. The substances whose concentration is to be reduced may also be of bacterial origin, namely both Gram-negative and Gram-positive bacteria, for example, endotoxins (lipopolysaccharides), or enterotoxins, for example, toxic shock syndrome toxin-1 (TSST-1) as well as *Staphylococcus aureus* and staphylococcal enterotoxin B (SEB).

The reduction in concentration is especially preferably performed on whole blood or blood plasma.

The device (1) according to the invention is described below on the basis of a nonrestrictive example using the preferred dimensions.

The separation device (1) consists of a hollow cylindrical inner housing (9) having a diameter of 6.2 cm on the average. The filling connection (7) for filling the separation device (1) with the separation medium or adsorbent is arranged tangentially on the inner housing (9). The filling connection (7) protrudes out of the inner housing (9) by a length of 16.5 mm. To fill the separation device, a hose line (8) is inserted into the filling connection (7). In addition to mounting elements (17) in the form of snap connections, which are arranged vertically opposite one another in pairs and serve to align the radial fluid inlet (5) and the radial fluid outlet (6) in arrangements one above the other, are also mounted on the inner housing (9). Accordingly, receiving elements (18) for the mounting elements (17) are mounted in the housing end caps (3, 4). The cut and welded hose line (8) extends at most from its length up to the opposing mounting elements (17). The inner housing (9) and the hose line (8) are surrounded by two housing outer wall segments (11). The two housing outer wall segments (11) are connected to one another via a catch mechanism (12) in the form of a snap connection, each housing outer wall segment (11) having a catch element (13) and a receiving element (14). There is a distance of 6.4 mm between the inner housing (9) and the housing outer wall segments (11). For stabilization of the housing outer wall segments (11), spacer elements are provided on the inside to stabilize the housing outer wall segments (11), corresponding essentially to the distance between the inner housing (9) and the housing outer wall segments (11).

The invention claimed is:

1. A separation device comprising
a hollow cylindrical detachable outer housing sealed at a top side by a top end cap and at a bottom side by a bottom end cap wherein the hollow cylindrical detachable outer housing further comprises a plurality of housing outer wall detachable segments connected together by at least one catch element and at least one receiving element,
a fluid inlet,
a fluid outlet,
an inner housing enclosed within the hollow cylindrical detachable outer housing, and
a filling connection for a separation medium tangentially attached to the inner housing at a side thereof and arranged tangentially to, and enclosed within, the hollow cylindrical detachable outer housing.

2. The separation device according to claim 1, characterized in that
a hose line for filling the separation device is mounted on the filling connection.

3. The separation device according to claim 1, characterized in that
each of the top end cap and the bottom end cap has radially displaced therein the fluid inlet and the fluid outlet, respectively.

4. The separation device according to claim 3, characterized in that
the top and bottom end caps are attached to the inner housing in such a way that the fluid inlet and the fluid outlet point in a predetermined direction arranged in the same plane.

5. The separation device according to claim 4, characterized in that
mounting elements locking the top and bottom end caps in place are provided on the inner housing.

6. The separation device according to claim 5, characterized in that
receiving elements are provided in an edge area of the top and bottom end caps formed as recesses or indentations in the top and bottom end caps to receive the mounting elements provided on the inner housing.

7. The separation device according to claim 3, characterized in that
a hose line for filling the separation device is mounted on the filling connection.

8. The separation device according to claim 1, characterized in that
the detachable segments are clamped or locked between the top and bottom end caps.

* * * * *